United States Patent [19]

Jacobs et al.

[11] 4,447,445

[45] May 8, 1984

[54] MANOALIDE, AN ANTI-INFLAMMATORY ANALGESIC MARINE NATURAL PRODUCT

[75] Inventors: Robert S. Jacobs, Santa Barbara; D. John Faulkner, La Jolla, both of Calif.

[73] Assignee: The Regents of the University of Calif., Berkeley, Calif.

[21] Appl. No.: 519,852

[22] Filed: Aug. 3, 1983

[51] Int. Cl.$^3$ ............................................ A61K 31/335
[52] U.S. Cl. .................................................... 424/279
[58] Field of Search ....................................... 424/279

[56] References Cited

PUBLICATIONS

Chem. Abst., vol. 93, (1980)–168442Q.

Primary Examiner—Stanley J. Friedman
Attorney, Agent, or Firm—Joseph E. Mueth

[57] ABSTRACT

The method of treating mammals including humans in need of a drug having analgesic and/or anti-inflammatory activity comprising the administration of a therapeutically effective amount of manoalide, seco-manoalide or dehydro-seco-manoalide. The anti-inflammatory utility includes acute, chronic and delayed sensitization inflammatory processes.

6 Claims, 9 Drawing Figures

Figure 7:
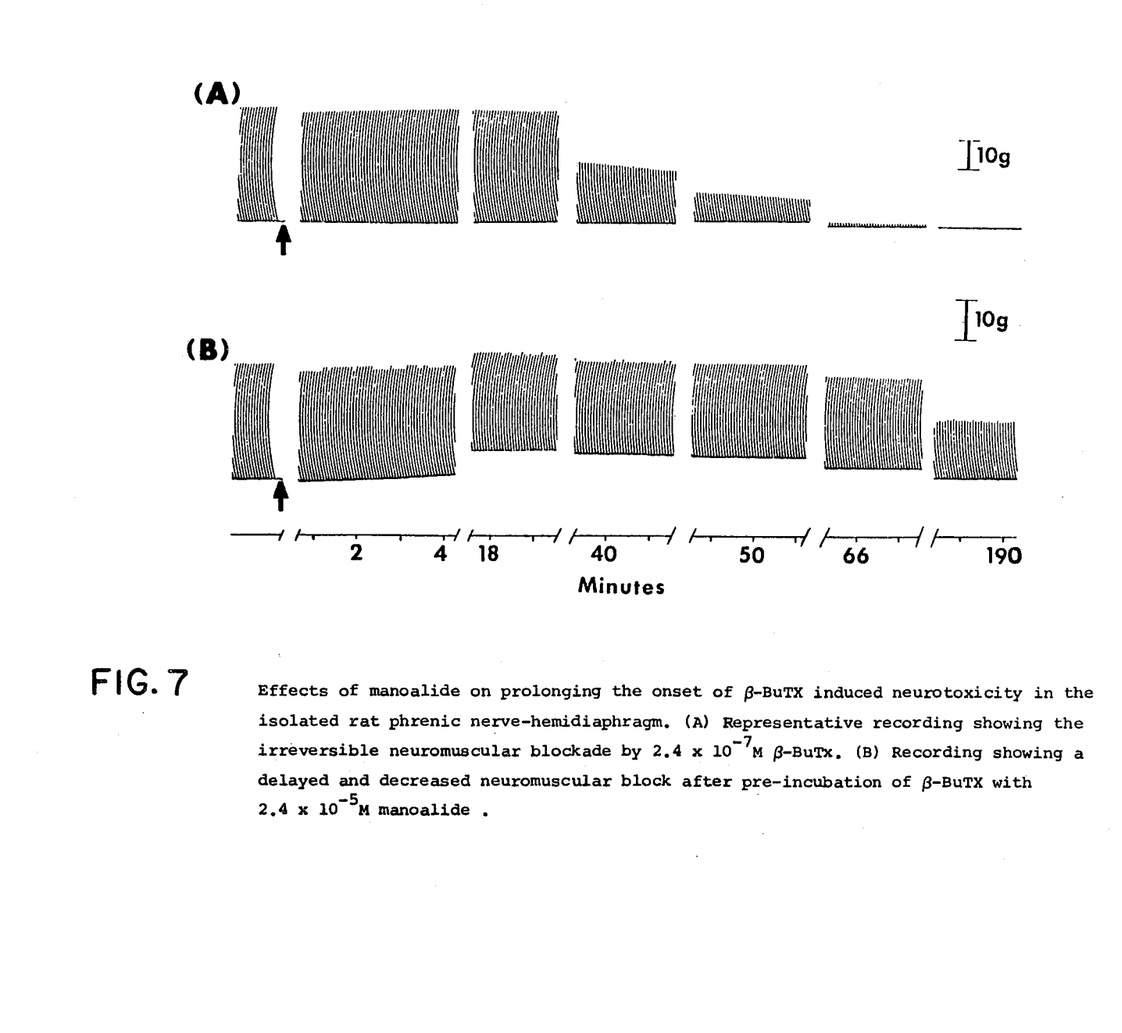

FIG. 7  Effects of manoalide on prolonging the onset of $\beta$-BuTX induced neurotoxicity in the isolated rat phrenic nerve-hemidiaphragm. (A) Representative recording showing the irreversible neuromuscular blockade by $2.4 \times 10^{-7}$ M $\beta$-BuTX. (B) Recording showing a delayed and decreased neuromuscular block after pre-incubation of $\beta$-BuTX with $2.4 \times 10^{-5}$ M manoalide.

DOSE – RESPONSE CURVE – INHIBITION OF PURIFIED PHOSPHOLIPASE $A_2$ BY MONOALIDE. MANOALIDE WAS PREINCUBATED WITH PURIFIED BEE VENOM FOR 1 HOUR, THEN ADDED TO PHOSPHATIDYCHOLINE (1.36mM) AND INITIAL VELOCITY OF HYDROLYSIS WAS MEASURED. MANOALIDE'S $K_I = 5 \times 10^{-7}$M. THIS REACTION WAS RUN AT 41°C, pH = 7.4.

FIG. 8

FIG. 9

MANOALIDE, AN ANTI-INFLAMMATORY ANALGESIC MARINE NATURAL PRODUCT

This invention was made with Government support under Sea Grant No. NA 80 AA-D-00120, Project No. R/MP-21, awarded by the National Oceanic & Atmospheric Administration. The Government has certain rights in this invention.

BACKGROUND OF THE INVENTION

Manoalide, from the marine sponge *Luffariella variabilis* (POLEJAEFF) has been reported by E. D. de Silva and P. J. Scheuer; Tetrahedron Letters Vol. 21, pp 1611–1614 Pergamon Press Ltd. 1980. The structure of this compound is as follows:

Seco-manoalide is described in E. D. DeSilva and P. J. Scheuer, Tetrahedron Letters Vol. 22, pp 3147–3150 (1980). Dehydro-seco-manoalide is obtained from the above-identified marine sponge and is recovered from the fraction slightly less polar than and preceding manoalide.

Manoalide is a non-steriod and it has now been discovered to be an anti-inflammatory and analgesic agent. Its potency has been found to be greater than that of indomethacin and its site of action in the inflammatory process is different from that of indomethacin. While it is less potent than hydrocortisone, manoalide possesses a pharmacological spectrum different from the glucocorticoids. Uses include treatment of rheumatoid arthritis, osteoarthritis, rheumatic carditis, collagen and/or auto-immune diseases such as myasthenia gravis, allergic diseases, bronchial asthma, and ocular and skin inflammatory diseases. Manoalide appears to be devoid of the endocrine properties of the glucocorticoids yet still appears anti-inflammatory and immunosuppressive. As such, it may also be useful as adjuvant therapy associated with organ and tissue transplants and any neurological disease involving metabolism of nervous tissue phospholipid such as multiple sclerosis. Because of its selective antagonism of chemical irritation (i.e. PMA inflammation) and the fact that it prevents the paralytic action of $\beta$-bungarotoxin, manoalide can be useful in the treatment of venoms such as certain snake and insect bites, bee or wasp stings or any venom in which a major constituent is the enzyme phospholipase $A_2$. Since manoalide blocks oxazolone induced inflammation this compound would be useful in treating forms of allergic contact dermatitis (such as poison oak or poison ivy).

Accordingly, it is believed that this invention makes a significant advance in the pharmaceutical arts.

SUMMARY OF THE INVENTION

Briefly, the present invention comprises the method of treating mammals including humans in need of a drug having analgesic and/or anti-inflammatory activity comprising the administration of a therapeutically effective amount of manoalide, seco-manoalide or dehydro-seco-manoalide.

It is an object of this invention to provide a novel therapeutic method.

More particularly, it is an object of this invention to provide an improved therapy involving anti-inflammatory and analgesic properties.

These and other objects and advantages of this invention will be apparent from the detailed description which follows.

Manoalide, seco-manoalide or dehydro-seco-manoalide are administered to mammals including humans in an effective amount on the order of 10 to 50 mg per day per kilogram of body weight. The drug may be administered orally, parenterally, or by other standard administration routes. The dosage form may be by tablet containing normal acceptable additives, excipients, etc. The parenteral form contains typical aqueous intravenous solution ingredients.

The marine natural products seco-manoalide and dehydro-seco-manoalide having the structure shown below have been found to have anti-inflammatory activity in the PMA-mouse ear assay. In preliminary testing, this activity was found to be nearly equivalent in potency to that of manoalide. These comounds had no significant activity in preliminary assays for: inhibition of cell division, effects on cardiac muscle, or effects on skeletal muscle.

SECO - MANOALIDE

DEHYDRO - SECO - MANOALIDE

Spectral characteristics of Dehydro-seco-manoalide: oil; UV (EtOH) 316 nm ($\epsilon$ 12000), 205 nm ($\epsilon$ 10300); UV (EtOH+NaOH) 461 nm ($\epsilon$ 25000), 280 nm ($\epsilon$ 1600), 246 nm ($\epsilon$ 2000); $^1$H NMR (CDCl$_3$) $\delta$ 0.96 (s, 6 H), 1.56 (s, 3H), 1.60 (s, 3H), 5.11 (bt, 1H, J=7 Hz), 6.14 (s, 1H), 6.32 (s, 1H), 6.82 (d, 1H, J=16 Hz), 6.91 (d, 1H, J=6 Hz), 7.34 (dd, 1H, J=16, 6 Hz), 9.52 (s, 1H); $^{13}$C NMR (CDCl$_3$) $\delta$ 194.3, 171.5, 160.0, 146.3, 145.8, 137.8, 136.8, 133.8, 128.3, 126.9, 121.8, 119.5, 97.8, 40.1, 39.7, 34.8, 32.6, 29.5, 28.5, 27.7, 27.2, 24.6, 19.7, 19.4, 16.0.

DESCRIPTION OF THE PREFERRED EMBODIMENTS

A. Acute Toxicity

Test compound is injected subcutaneously into mice which are observed for three days for both lethality and any unusual behavior or appearance. This assay may be performed in conjunction with analgesia assays.

B. Analgesia—Phenylquinone Writhing Assay

Test compound is injected subcutaneously into mice. After 30 minutes, phenylquinone is injected intraperitoneally to cause pain as indicated by writhing.

Absence of or a statistically significant decrease in writhing is considered evidence of analgesia [Hendershot, L. C. and G. Forsaith, Pharmacol. Exp. Ther. 125, 237 (1959)].

C. Analgesia—Haffner Technique

Analgesia is measured as the lack of response to a pinch clamp applied to the tail of a mouse 15 to 30 minutes following subcutaneous injection of the test compound [Bianchi, G. and G. Franeschini, Brit. J. Pharmac. 9, 280 (1954)].

D. Electrically Stimulated Guinea Pig Ileum

Test compound is administered to an electrically driven section of isolated small intestine and observed for its ability to mimic, antagonize or potentiate the effects of morphine or nalorphine [Gyang, E. A. and H. W. Kosterlitz, Br. J. Pharmac. Chemother. 27, 514 (1966)].

E. Mouse Ear Anti-Inflammatory Assay

Test compound and phorbol myristate acetate (PMA) or arachidonic acid (ARA) are topically applied simultaneously to the left ears of mice. Three hours 20 minutes (or one hour for ARA) after application, the mouse is sacrificed, left and right ears removed and standard sized bores taken. Edema (inflammation) is measured as the difference in weight between left and right ears [Van Arman, C. G., Clin. Pharmacol. Ther. 16, 900–904 (1974)].

F. Rat Uterus

Test compound is administered to the isolated rat uterus and observed for its ability to mimic, antagonize or potentiate the effects of prostaglandins [modified from DeJalon, Bayo and DeJalon, Farmacoter Act. 3, 313 (1945)].

G. Rat Phrenic Nerve—Hemidiaphragm

Compound is tested for its ability to inhibit or facilitate the twitch of the isolated diaphragm in response to the electrical stimulation of the phrenic nerve [Bülbring, E., Br. J. Pharmac. Chemother. 1, 38 (1946)].

H. Eight Day Administration

Test compound is administered to mice subcutaneously once per day for seven days. On the eighth day, blood, organ and tissue samples are taken from each animal and analyzed for differences relative to controls.

I. Histology

Mouse ears from the anti-inflammatory assay are fixed in Karnofsky's fixative and osmium tetroxide and then embedded in araldite epoxy resin for sectioning for light and electron microscopy.

Other Methods

A. Fertilized Sea Urchin Egg Inhibition of Cleavage Assay

Test compound is added to a slurry of eggs (from *Lytechinus pictus*) within five minutes following fertilization and incubated until the completion of first division in control slurry, approximately 90 minutes. Inhibition is measured as the percent of undivided eggs in the slurry at the end of incubation [Hinegardner, R., In *The Sea Urchin Embryo*, ed. C. Czihar (Springer-Verlag, Berlin, 1974)].

B. Guinea Pig Auricles

Test compound is administered to the spontaneous beating isolated guinea pig auricles and observed for its ability to alter either the rate or the force of contraction or to antagonize the effects of acetylcholine [modified from J. Physiol. 61, 547 (1926); Heffter's Hanb. Exp. Pharmak. 4, 185 (1937)].

C. Guinea Pig Illeum

Test compound is administered to an isolated section of small intestine and observed for its ability to mimic, antagonize or potentiate the effects of either histamine or acetylcholine [Pflugers Arch. ges Physiol. 102, 123 (1940)].

D. Acetylcholinesterase Assay

Test compound is incubated with rat brain extract (source of acetylcholinesterase), acetylthiocholine and dithiobis (2-nitrobenzoic acid). Inhibition of acetylcholinesterase activity is measured spectrophotometrically.

E. Tumor Promotion

An initiating agent, 7,12-dimethylbenzanthracene (DMBA), is applied topically to the ears of mice. Beginning one month later, a tumor promoting agent, phorbol myristate acetate (PMA), and the test compound are applied simultaneously to the ears twice per week for four weeks, then once per week for two weeks. Ears are observed for formation of tumors at the times of application and one week following completion of applications.

F. Oxazolone-Induced Sensitization

Mice are sensitized by the application of oxazolone to the abdominal area. One week later, test compound and oxazolone are topically applied to the ears of these mice. Six hours after application, the mice are sacrificed, the ears removed and standard sized bores taken and weighed. Edema (inflammation) is measured as the difference in weight between control and treated ears. Without previous sensitization exposure, oxazolone has no inflammatory effect on mouse ears.

Results

Manoalide was subjected to pharmacological evaluation. Initial results were as follows:

Analgesia—Phenylquinone Writhing—100% analgesia at 50 mg/kg, subcutaneous administration.

The discovery that manoalide was active against chemically-induced pain led to extensive study of the compound.

Figure 1:
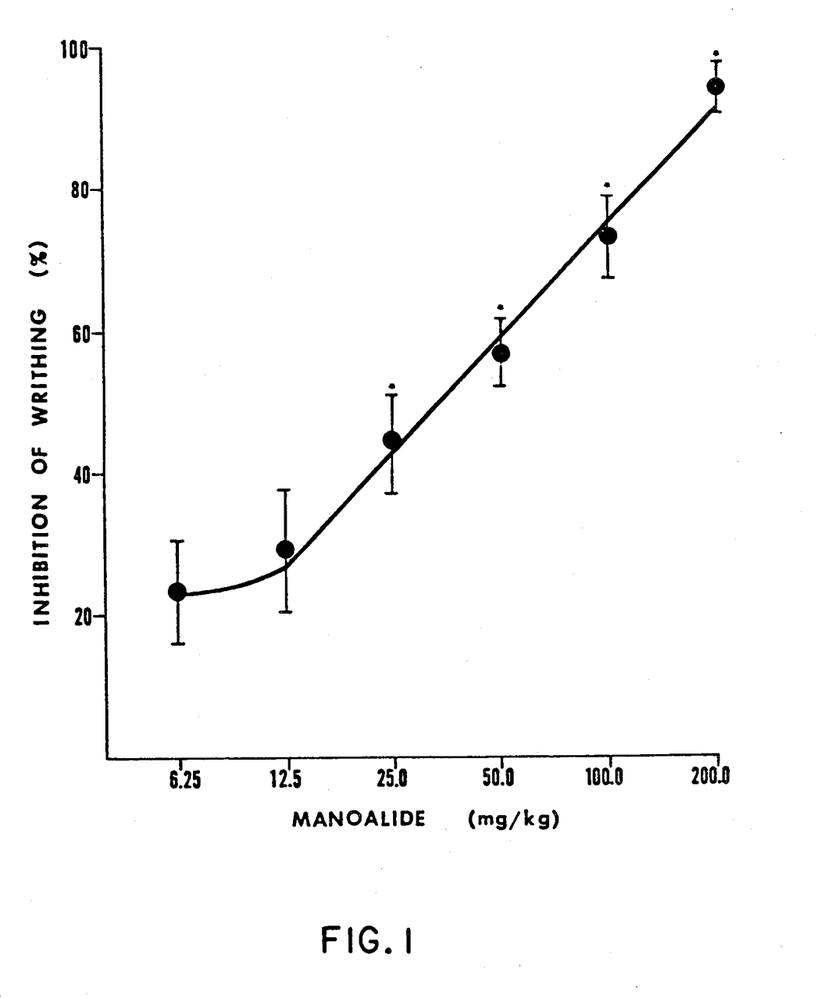

The onset of action or manoalide was delayed in comparison to other standard analgesics: the peak effect was detected about two hours after administration. The $ED_{50}$ for manoalide is approximately 40 mg/kg when administered subcutaneously (FIG. 1). For comparison purposes, the $ED_{50}$ for morphine is about 0.6 mg/kg and for indomethacin is about 5 mg/kg under the same conditions.

On the basis of these results, experiments were conducted to determine if manoalide's analgesic action was similar to indomethacin (i.e., anti-inflammatory) or whether it was similar to morphine (i.e., a narcotic analgesic).

In studies utilizing the electrically driven ileum, it was found that manoalide neither blocked electrically induced contractions, an effect common to both morphine and the endorphins, nor did it antagonize the morphine block as would be expected if it had properties common to nalorphine. Similarly, high doses of manoalide did not significantly affect mechanically induced pain as tested by the Haffner technique. Thus far, it is only active against chemically induced pain and therefore is pharmacologically distinct from the narcotics.

Figure 2:
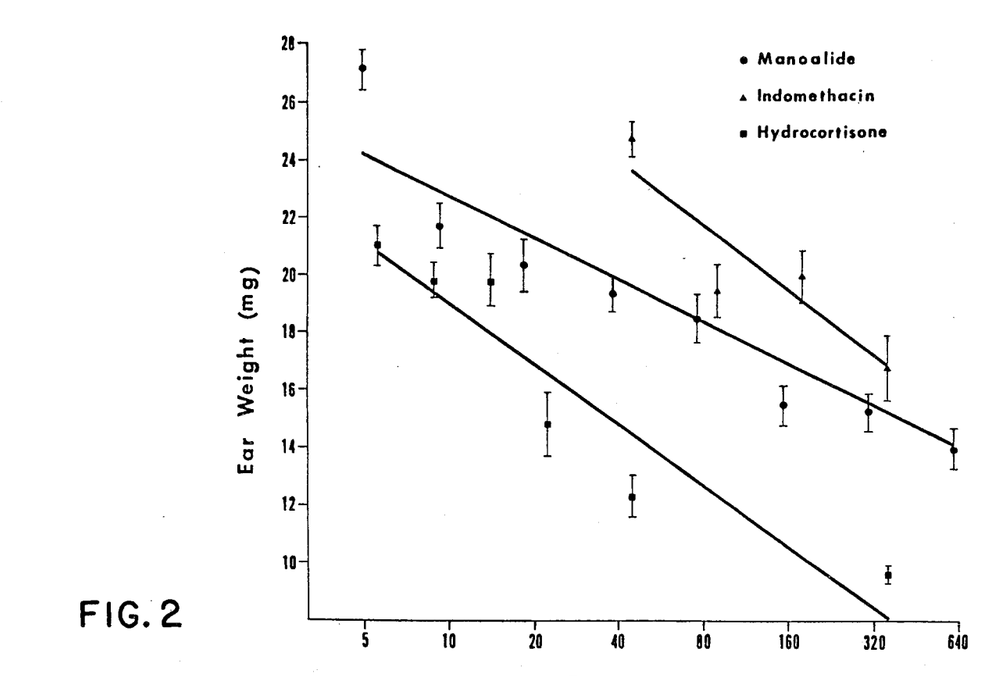
Figure 3:
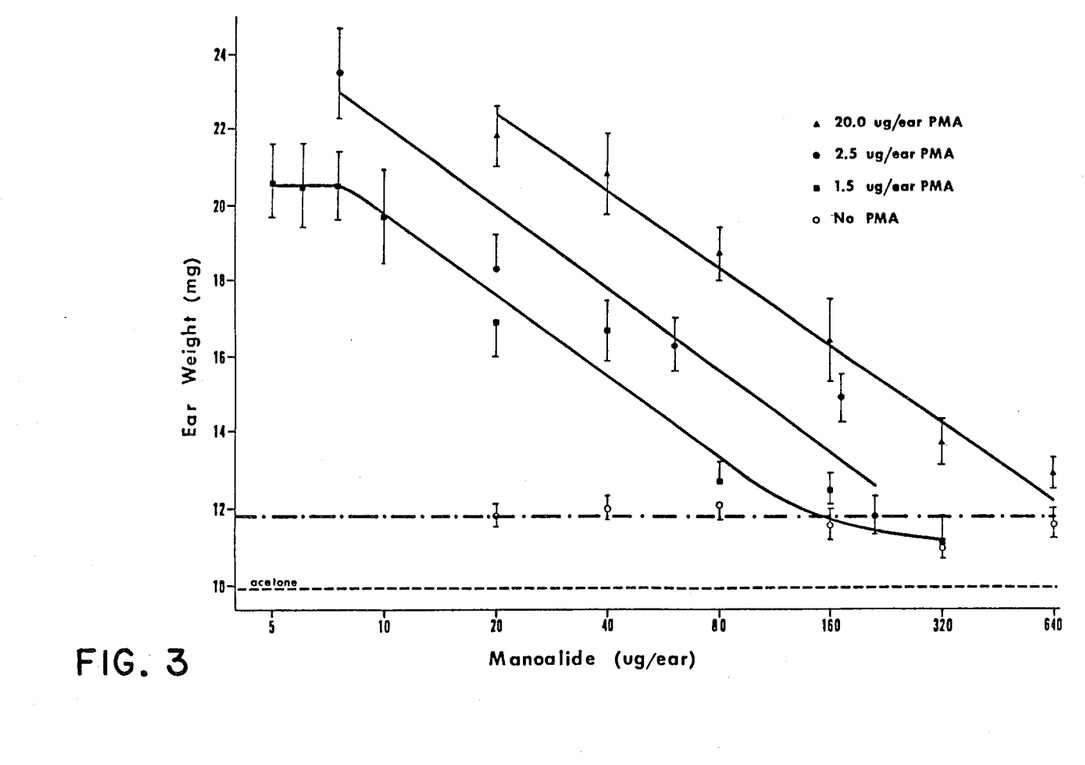

In the presence of manoalide, there was a marked reduction of inflammation due to PMA induction when a total dose of 10 μg was applied to the ear. An approximate $ED_{50}$ is 40 μg/ear (FIG. 2) (will vary with PMA dose, FIG. 3). Histological examination of the ears indicated that manoalide qualitatively produced similar effects to both hydrocortisone and indomethacin. Quantitatively, manoalide was more potent than indomethacin and less potent than hydrocortisone (FIG. 2). The combination of indomethacin and manoalide or hydrocortisone and manoalide resulted in a potentiation of the inhibition of edema indicating a novel mechanism of action (Table II).

TABLE I
Summary of Manoalide Studies

| Assay | Remarks |
|---|---|
| Initial Screening: | |
| Fertilized Sea Urchin Egg Inhibition of Cleavage | Active |
| Guinea Pig Auricles | Active |
| Mouse Toxicity and Analgesia | Active |
| Guinea Pig Ileum | Active |
| Rat Phrenic Nerve - Hemidiaphragm | Active |
| Dose Response Studies: | |
| Analgesia (Phenylquinone Writhing) | $ED_{50}$ = 40 mg/Kg |
| Fertilized Sea Urchin Egg | $ED_{50}$ = 1.0 microgram/ml |
| PMA - Mouse Ear Anti-inflammatory | $ED_{50}$ = 40 microgram/ear |
| Investigative Assays: | |
| Electrically Stimulated Guinea Pig Ileum | Inactive |
| Analgesia (Haffner Tail-Clip) | Inactive |
| Rat Uterus (Prostaglandin Assay) | Inactive |
| PMA - Mouse Ear Potentiation (with Hydrocortisone and Indomethacin) | Active |
| Acetylcholine Antagonism in Guinea Pig Auricles | Inactive |
| Arachadonic Acid - Mouse Ear | Inactive |
| PMA - Mouse Ear Time Course of Action | Optimum activity at less than 5 minutes post treatment |
| Acetylcholinesterase | Inactive |
| PMA - Mouse Ear Competition for binding | Does not compete directly with PMA |
| Eight day administration | Non-toxic; no glucocorticoid (steroid-like) properties |
| Rat Phrenic Nerve-Hemidiaphragm with β-Bungarotoxin | Inactivates the irreversible neurotoxic action of β-Bungarotoxin |
| Histology (methodology) (summary master degree paper) | Decreased lymphocyte and PMN infiltration |
| PMA = Mouse Ear anti-inflammatory | Active |
| Inhibition of purified phospholipase $A_2$ | Active |

TABLE II
Mouse Ear Edema Potentiation Studies

| % Inhibition of Edema Alone | Manoalide 0.04 mg/ear A | Hydrocortisone 0.009 mg/ear B | Indomethacin 0.09 mg/ear C |
|---|---|---|---|
| | 28.24 ± 6.58 | 16.59 ± 7.00 | 31.42 ± 12.72 |
| % Inhibition of Edema Additive | A + B | B + C | A + C |
| Expected | 44.83 | 48.01 | 59.66 |
| Observed | 66.83 ± 5.06 | 75.84 ± 7.01 | 83.31 ± 2.99 |

(Eight animals in each experiment)

The next question pursued was whether manoalide had a mechanism of action similar to hydrocortisone or to indomethacin. In this case, the working hypothesis was based on the mechanism of action of PMA induced inflammation.

PMA causes the release of arachidonic acid (ARA) from lysosomes. The released ARA is the substrate for the synthesis of prostaglandins which are believed to contribute to pain and inflammation. It is thought that hydrocortisone exerts its anti-inflammatory effect in part by "stabilizing lysosomes" and thereby preventing release of ARA. On the other hand, indomethacin acts to inhibit prostaglandin synthetase and by this mechanism prevents formation of prostaglandins.

Figure 4:
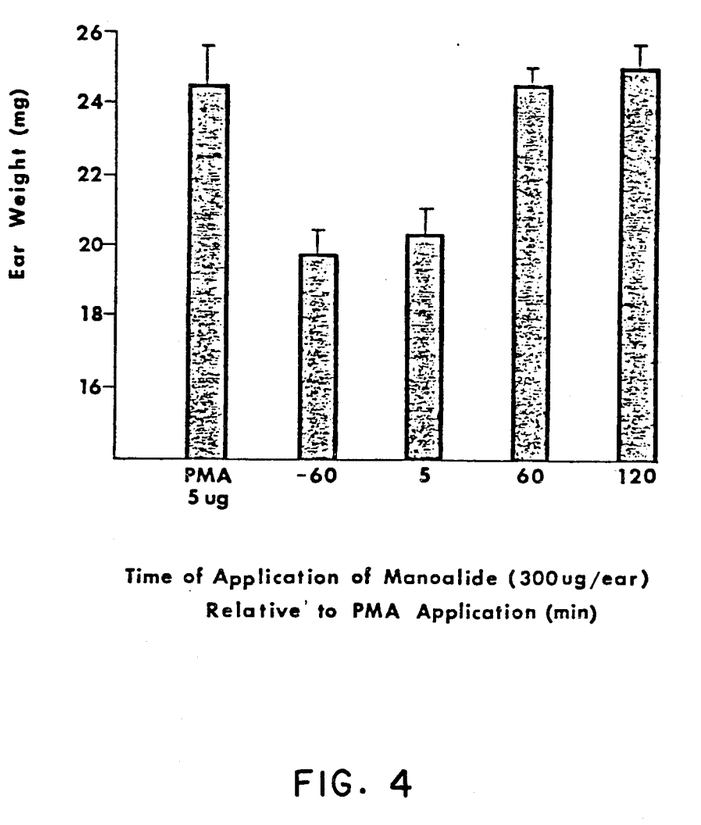

ARA induced inflammation was effectively blocked by indomethacin over the same dosage range as PMA induced inflammation, as would be expected if prostaglandin synthetase was inhibited. Neither manoalide nor hydrocortisone affected the ARA induced inflammation at any of the doses employed, suggesting that manoalide acts at a site prior to prostaglandin synthesis. Direct interaction of manoalide with prostaglandins ($PGE_2$, $PGE_1$ and $PGF_2$) was ruled out when it was shown to be inactive against these agents in the rat uterus preparation. Time course studies showed that manoalide was most effective when applied within five minutes of PMA application (FIG. 4).

To differentiate between the spectrum of activity of manoalide versus that of hydrocortisone, a seven day systemic administration of manoalide (50 mpk) or hydrocortisone (25 mpk) was given to immature mice. (Table III)

TABLE III
7 Day Manoalide Treatment 50 mpk

| Treatment | Group A Control | Group B Manoalide | Group C Hydrocortisone |
|---|---|---|---|
| Dose | 0.1 ml/10 g sesame oil | 50 mg/kg | 25 mg/kg |
| Lethality | 0 | 3.8–37.5% | 0 |
| N | 7 | 4 | 7 |
| | Mean | Mean | Mean |
| Body Weight | | | |
| day 0 (g) | 17.9 | 18.3 (+2.2) | 18.1 (+1.1) |
| day 7 (g) | 25.7 | 26.3 (+2.3) | 22.3 (−13.2) |
| Acute Inflamation with PMA (mg) | 13.5 | 15.5 (+14.8) | — |
| Organ Wts % of Body wgt. | | | |
| Liver | 5.80 | 6.32 (+8.9) | 5.67 |
| Spleen | 0.48 | 0.83 (+71.7) | 0.17 (−63.8) |
| Kidney | 1.41 | 1.28 (−9.2) | 1.63 (15.8) |
| Testes | 0.53 | 0.49 (−6.5) | 0.62 (+18.1) |

TABLE III-continued

7 Day Manoalide Treatment 50 mpk

| Treatment | Group A Control | Group B Manoalide | Group C Hydrocortisone |
|---|---|---|---|
| Thymus | 0.45 | 0.37 (−18.4) | 0.08 (−81.6) |
| Heart | 0.42 | 0.35 (−17.7) | 0.56 (+32.4) |
| Adrenal (mg % pair) | 13.9 | 18.41 (+32.3) | 11.01 (−20.9) |
| Food Consumption | | | |
| mean g/mouse/day | 5.89 | 5.47 (−7.1) | 6.69 (+13.6) |
| H$_2$O Consumption | | | |
| ml/mouse/day | 8.1 | 6.1 (−25.7) | 9.8 (+21.0) |
| Blood Analysis | | | |
| wbc/mm$^3$ mean | 1667 | 8025 (+381.4) | 2850 (+71.0) |

Following this treatment, blood samples were taken and autopsies were performed. In brief, hydrocortisone produced the expected thymus involution and reduction of adrenal gland, spleen weights and body weight. In contrast, treatment with manoalide only slightly decreased thymus weight and size, did not alter adrenal gland weight and markedly enlarged the spleen. The animals grew to normal body weight. Manoalide appeared to be acutely immunosuppressive in that injection wound sites did not heal. Finally, manoalide produced a 400% increase in white blood cell count (sbc) over control whereas hydrocortisone did not. Thus, there is evidence that manoalide is inducing an immune response in mice, different than that induced by hydrocortisone.

Figure 5:
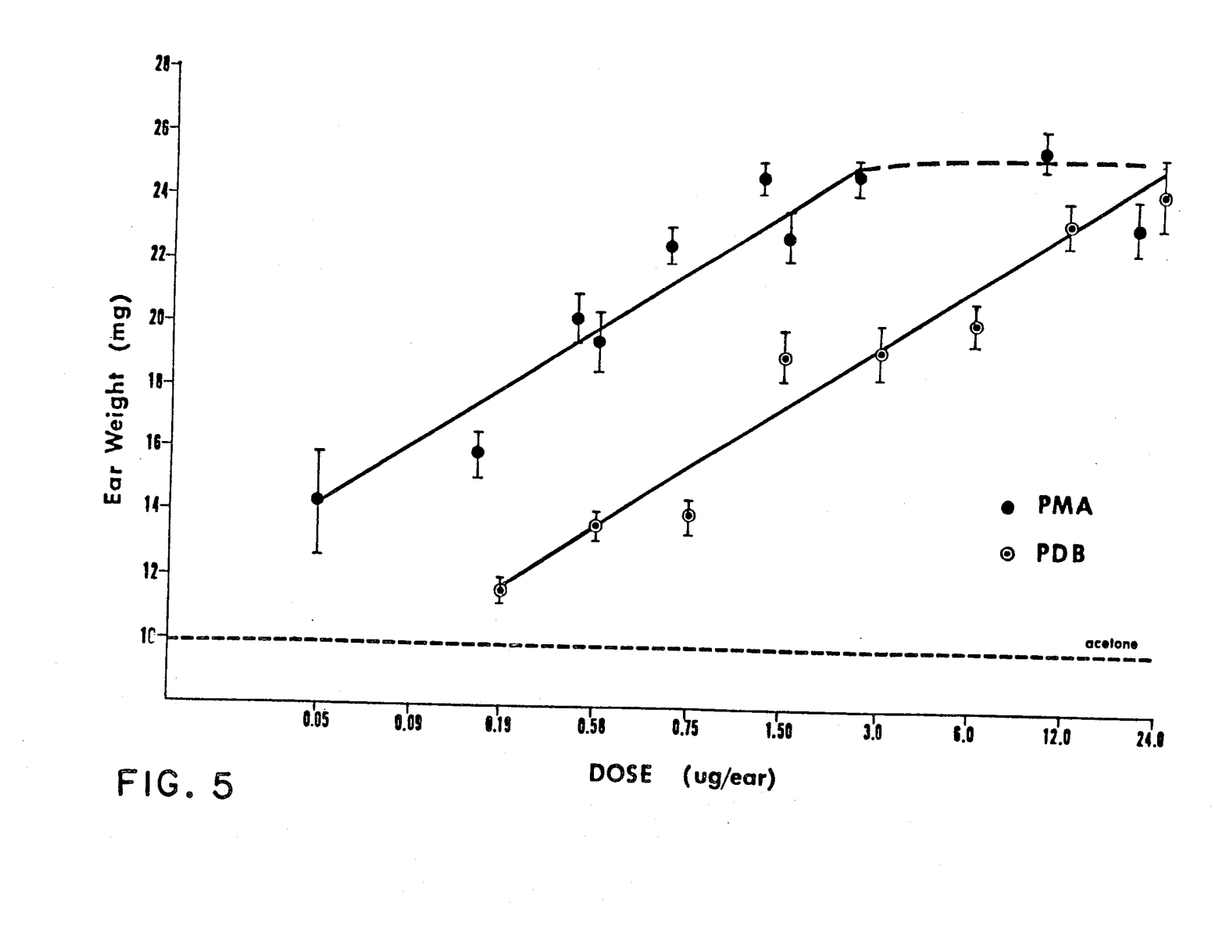
Figure 6:
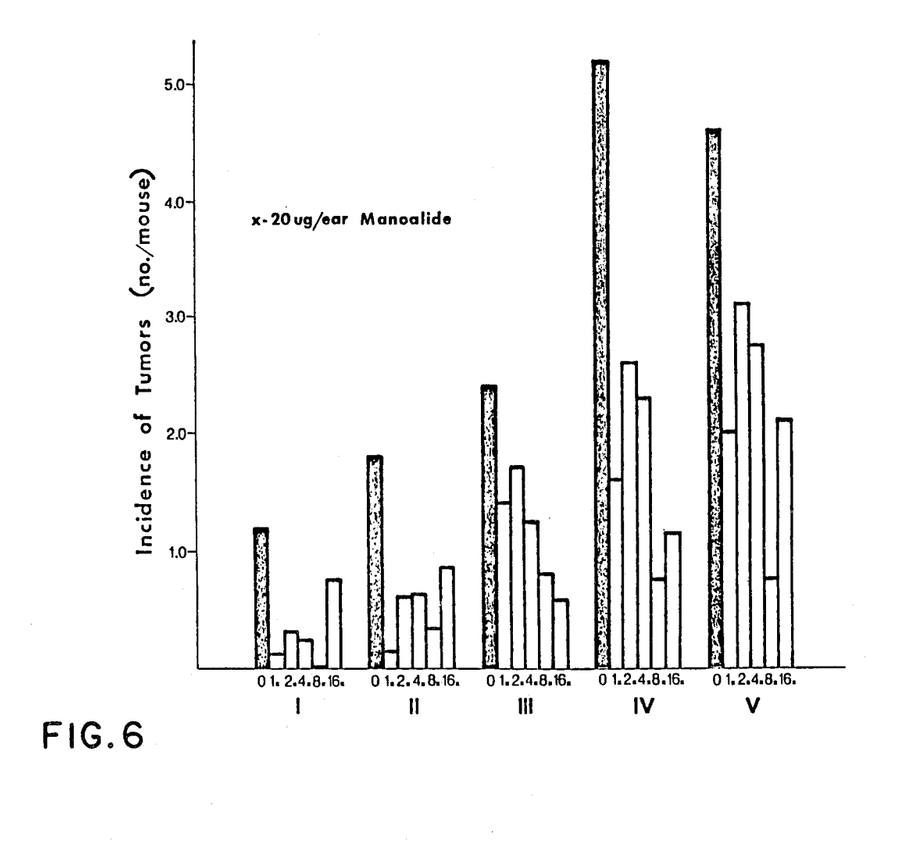

A concurrent line of investigation concerned another effect of the phorbol esters, tumor promotion. Of the phorbols which cause inflammation and promote tumor formation, PMA is the most potent inflammatory agent (FIG. 5). Manoalide not only blocks this inflammation, but also significantly decreases the incidence of tumors formed on mouse ears using PMA as promoter in conjunction with the initiator DMBA (FIG. 6).

Manoalide produces a modest contracture in the rat hemidiaphragm preparation as well as mildly inhibiting the directly stimulated twitch. To investigate a possible phospholipase A$_2$ inhibition by manoalide, competition against β-bungarotoxin action on the diaphragm was investigated. In these studies it was found that manoalide inactivated the irreversible neurotoxic action of β-bungarotoxin (Table IVa). This is a direct reaction with the toxin requiring pre-incubation (Table IVb).

TABLE IVa

Inactivation of β-BuTX paralysis by manoalide (pre-incubation one hour)

| Concentration | | | |
|---|---|---|---|
| Manoalide × 10$^{-5}$ | β-BuTX × 10$^{-7}$ | n | Mean TI$_{50}$ ± S.E. |
| 0.0 | 2.4 | (4) | 36.0 ± 4.2 |
| 0.6 | 2.4 | (4) | 45.2 ± 7.0* |
| 1.2 | 2.4 | (4) | 75.7 ± 16.5* |
| 2.4 | 2.4 | (5) | 137.0 ± 22.2* |

*statistically significant difference relative to β-BuTX alone, P < 0.05 unpaired students' t-test.

TABLE IVb

Effect of incubation time on β-BuTX$^+$ inactivation

| | | Mean TI$_{50}$ ± S.E. | | |
|---|---|---|---|---|
| Pre-incubation time (min.) | n | manoalide 2.4 × 10$^{-5}$ M | n | mepacrine 2.1 × 10$^{-5}$ M |
| 0 | (3) | 64.60 ± 6.03 | (2) | 43.50 ± 2.50 |
| 15 | (4) | 83.20 ± 6.65* | | |
| 30 | (5) | 79.10 ± 3.46* | (2) | 49.00 ± 4.00 |

TABLE IVb-continued

Effect of incubation time on β-BuTX$^+$ inactivation

| | | Mean TI$_{50}$ ± S.E. | | |
|---|---|---|---|---|
| Pre-incubation time (min.) | n | manoalide 2.4 × 10$^{-5}$ M | n | mepacrine 2.1 × 10$^{-5}$ M |
| 60 | (7) | 140.50 ± 18.90* | (3) | 46.60 ± 7.54 |
| 120 | (5) | 156.60 ± 22.50* | (3) | 35.66 ± 4.67 |

*Statistically significant difference relative to controls (zero), P < 0.5 unpaired students' t-test
$^+$5 μg/ml β-BuTX.

Another study involves the effect of manoalide on an inflammatory response which requires previous sensitization. Manoalide inhibits local, topical inflammation and the possibility that it also may inhibit sensitization has been investigated. It was found that manoalide blocks the oxazolone induced inflammation (Table V).

Addendum to Activity of Manoalide

Figure 8:
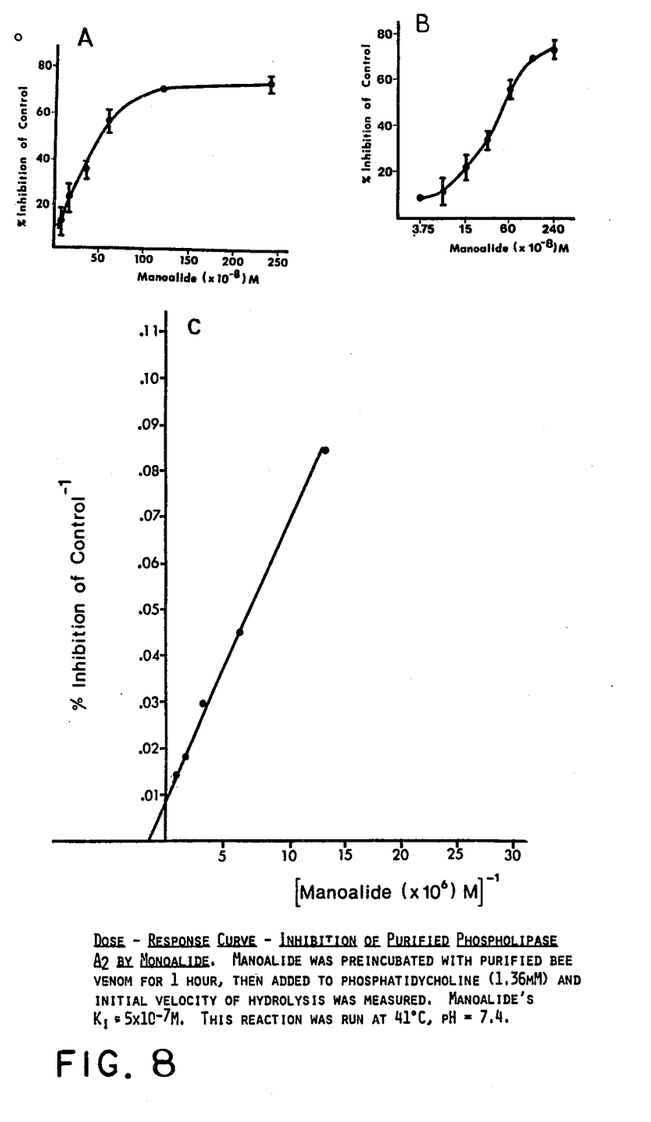

Purified phospholipase A$_2$ from bee venom was incubated with phosphatidylcholine (1.36 mM). Initial velocity of hydrolysis was measured via a pH state (radiometer) as the amount of 0.005 N NaOH consumed per minute. Varying concentrations of manoalide were preincubated with PLA$_2$ for one hour and compared to solutions preincubated with no manoalide. Manoalide caused a concentration dependent decrease in enzyme activity (FIG. 8). Mepacrine, a PLA$_2$ antagonist, at concentrations as high as 10$^{-2}$ M was ineffective in this protocol. Thus, it appears that manoalide is a potent inhibitor of the hydrolysis of phosphatidylcholine.

Figure 9:
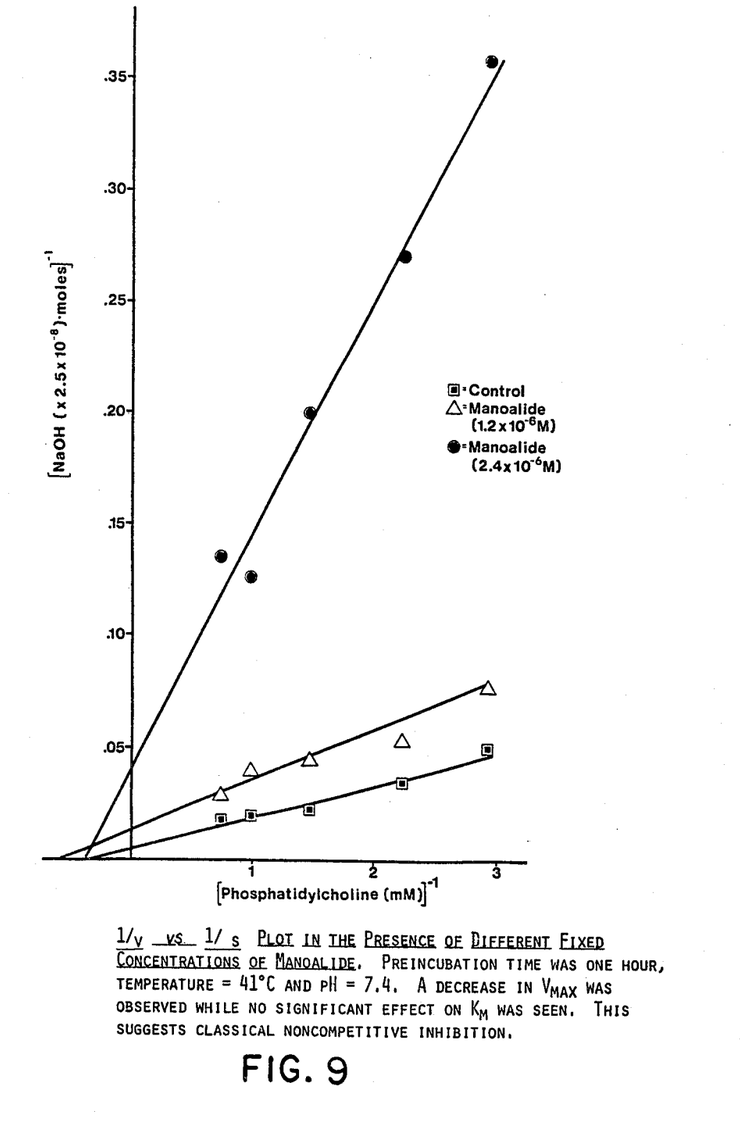

In experiments designed to explore the mechanism of action of manoalide in vitro, it was found that this compound is a non-competitive inhibitor of the enzyme phospholipase A$_2$ (FIG. 9).

TABLE V

INHIBITION OF OXAZOLONE-SENSITIZATION INFLAMMATION

| COMPOUND | DOSE | N | EAR WEIGHT (MGS) |
|---|---|---|---|
| Oxazolone alone | | 5 | 17.7 ± 2.0 |
| Ox. + Manoalide | 50 μg/ear | 5 | 17.5 ± 3.7 |
| Ox. + Manoalide | 100 μg/ear | 5 | 13.1 ± 1.4* |
| Ox. + Indomethacin | 50 μg/ear | 15 | 16.6 ± 5.7 |
| Ox. + Indomethacin | 100 μg/ear | 10 | 11.1 ± 1.2* |
| Ox. + Hydrocortisone | 50 μg/ear | 10 | 9.7 ± 1.2* |
| Ox. + Hydrocortisone | 100 μg/ear | 10 | 9.2 ± 0.4* |

*Statistically significant difference relative to oxazolone control, p < .05 one tailed student's T-test.

Having fully described the invention it is intended that it be limited only by the lawful scope of the appended claims.

We claim:

1. The method of treating mammals including humans in need of a drug having analgesic and/or anti-inflammatory activity comprising the administration to said mammals of a therapeutically effective amount of manoalide, seco-manoalide or dehydro-seco-manoalide.

2. The method of claim 1 wherein the drug is manoalide.

3. The method of claim 1 wherein the drug is seco-manoalide.

4. The method of claim 1 wherein the drug is dehydro-seco-manoalide.

5. The method of claim 1 wherein the drug is administered orally.

6. The method of claim 1 wherein the drug is administered parenterally.

* * * * *

UNITED STATES PATENT AND TRADEMARK OFFICE
CERTIFICATE OF CORRECTION

PATENT NO. : 4,447,445
DATED : May 8, 1984
INVENTOR(S) : Robert S. Jacobs, et al It is certified that error appears in the above-identified patent and that said Letters Patent is hereby corrected as shown below:

In column 1, lines 17-26, please change:

""

to

--  --

UNITED STATES PATENT AND TRADEMARK OFFICE
CERTIFICATE OF CORRECTION

PATENT NO. : 4,447,445
DATED : May 8, 1984
INVENTOR(S) : Robert S. Jacobs, et al It is certified that error appears in the above-identified patent and that said Letters Patent is hereby corrected as shown below:

In column 2, lines 29-47, please change:

"

"

to

Signed and Sealed this

Fifth Day of August 1986

[SEAL]

Attest:

DONALD J. QUIGG

Attesting Officer    Commissioner of Patents and Trademarks